(12) United States Patent
Adams

(10) Patent No.: US 10,993,906 B2
(45) Date of Patent: *May 4, 2021

(54) MEDICAL IMPLANT

(71) Applicant: Robert W. Adams, Roseland, VA (US)

(72) Inventor: Robert W. Adams, Roseland, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/459,577

(22) Filed: Jul. 1, 2019

(65) Prior Publication Data

US 2019/0321287 A1 Oct. 24, 2019

Related U.S. Application Data

(63) Continuation of application No. 15/682,386, filed on Aug. 21, 2017, now Pat. No. 10,806,696, which is a continuation of application No. 14/585,531, filed on Dec. 30, 2014, now abandoned, application No. 16/459,577, which is a continuation of application No. 14/585,531, filed on Dec. 30, 2014, now abandoned.

(60) Provisional application No. 62/080,584, filed on Nov. 17, 2014, provisional application No. 62/028,907, filed on Jul. 25, 2014.

(51) Int. Cl.

| *A61K 9/00* | (2006.01) |
| *A61K 45/06* | (2006.01) |
| *A61K 31/4468* | (2006.01) |
| *A61K 31/485* | (2006.01) |

(52) U.S. Cl.
CPC ........ *A61K 9/0024* (2013.01); *A61K 31/4468* (2013.01); *A61K 31/485* (2013.01); *A61K 45/06* (2013.01)

(58) Field of Classification Search
CPC .. A61K 31/726; A61K 31/727; A61K 9/0019; A61K 9/0024; A61L 27/22; A61L 29/08; A61L 29/12; A61L 29/126; A61L 29/16
See application file for complete search history.

(56) References Cited

U.S. PATENT DOCUMENTS

| 4,983,182 A | 1/1991 | Kijima |
| 5,633,000 A | 5/1997 | Grossman et al. |
| 5,858,388 A | 1/1999 | Grossman et al. |
| 6,126,956 A | 10/2000 | Grossman et al. |

(Continued)

FOREIGN PATENT DOCUMENTS

| CA | 2886951 A1 | 4/2014 |
| CN | 1156400 A | 8/1997 |

(Continued)

OTHER PUBLICATIONS

Gunatillake et al. Biodegradable synthetic polymers for tissue engineering. European Cells and Material vol. 5. 2003 (p. 1-16).

(Continued)

*Primary Examiner* — Lakshmi S Channavajjala
(74) *Attorney, Agent, or Firm* — Novick, Kim & Lee, PLLC; Harold L. Novick

(57) ABSTRACT

An improved medical implant device directed to, inter alia, (i) avoiding unwanted initial drug "burst" problems, (ii) providing a more level amount of drug delivery, (iii) reducing blood clotting, (iv) reducing the amount of drug material that remains in the implant device, and/or (v) novel materials for an implant device.

15 Claims, 7 Drawing Sheets

(EMBODIMENT 1)

(56) References Cited

U.S. PATENT DOCUMENTS

| | | |
|---|---|---|
| 6,596,296 B1 | 7/2003 | Nelson et al. |
| 6,974,625 B2 | 12/2005 | Hunter et al. |
| 7,169,183 B2 | 1/2007 | Liu et al. |
| 8,114,383 B2 | 2/2012 | Bartholomaus et al. |
| 8,449,901 B2 | 5/2013 | Shanley et al. |
| 2001/0029351 A1 | 10/2001 | Falotico et al. |
| 2003/0007992 A1 | 1/2003 | Gibson |
| 2003/0158509 A1 | 8/2003 | Tweden et al. |
| 2003/0175410 A1 | 9/2003 | Campbell et al. |
| 2007/0003753 A1 | 1/2007 | Asgari |
| 2007/0116736 A1 | 5/2007 | Argentieri |
| 2007/0116738 A1 | 5/2007 | Mauriac et al. |
| 2007/0125247 A1 | 6/2007 | Kunstmann et al. |
| 2010/0196478 A1 | 8/2010 | Masters |
| 2010/0241071 A1 | 9/2010 | Atanasoska et al. |
| 2010/0303883 A1 | 12/2010 | Pollock et al. |
| 2011/0027339 A1 | 2/2011 | Mao |
| 2012/0034306 A1 | 2/2012 | Pollock et al. |
| 2012/0130339 A1 | 5/2012 | Farra |
| 2013/0236524 A1 | 9/2013 | Holl et al. |
| 2013/0266631 A1 | 10/2013 | Clay et al. |
| 2014/0099351 A1 | 4/2014 | Adams et al. |
| 2017/0348229 A1* | 12/2017 | Adams ............... A61K 31/485 |

FOREIGN PATENT DOCUMENTS

| | | |
|---|---|---|
| CN | 1812753 A | 8/2006 |
| CN | 101023893 A | 8/2007 |
| EP | 1772115 A1 | 4/2007 |
| WO | 03/017826 A2 | 3/2003 |

OTHER PUBLICATIONS

Edgar Martin et al., "Critical Evaluation of Biodegradable Polymers Used in Nanodrugs", International Journal of Nanomedicine, vol. 8(1), pp. 3071-3091 (Aug. 18, 2013).

Zern et al. Control Growth Factor Release Using a Self-Assembled, PLos, Jun. 2010, vol. 5, issue 6, 2010.

Arakawa et al., "Stoichiometry of heparin binding to basic fibroblast growth factor". Archives of Biochemistry and Biophysics, col. 308, No. 1, 1994.

Yoon et el. Heparin-immobilized biodegradable scaffolds for local and sustained release of angiogenic growth factor. Dec. 2006, J Biomedical materials Research Part A.

* cited by examiner

*(EMBODIMENT 1)*

*(EMBODIMENT 2)*

*(EMBODIMENT 3)*

*(EMBODIMENT 4)*

*(EMBODIMENT 5)*

MEDICAL IMPLANT

CROSS-REFERENCE TO RELATED APPLICATIONS

This is a continuation application of U.S. application Ser. No. 14/585,531 filed on Dec. 30, 2014, and of U.S. application Ser. No. 15/682,386 filed on Aug. 21, 2017, and claims benefit and priority to U.S. provisional patent application Nos. 62/028,907 filed on Jul. 25, 2014, and 62/080,584, filed on Nov. 17, 2014, the entire contents of which are hereby incorporated by reference. These applications and the present application are commonly and solely owned by applicant, Robert W. Adams.

FIELD

This non-provisional application is directed to (i) an improved subcutaneous medical implant for mammals, (ii) improved methods of subcutaneous medical implant drug delivery and (iii) methods for making the improved subcutaneous medical implant device. More specifically, this application is directed to a problem in existing drug implants where there is an initial drug "burst" that is higher than the desired drug delivery level. Although some flexibility in drug delivery levels is inherent with virtually all implants, a significant problem exists. This "initial burst" problem also may deleteriously impact the time period of drug delivery. Thus, it is a goal of this invention to provide an implant that improves the sustained release of one or more drugs over time in a controlled manner.

Further, another drug delivery problem relating to implants involves clotting (e.g., when implanting the device and/or during drug release). In particular, if the flow of drug(s) is impeded by clotting in or near the implant channel(s) and/or in or near the implant opening(s), then problems may be created in terms of the initial delivery of the desired drug materials to the patient. Also, subsequent clotting may impair later drug delivery. Further, clotting may lead to tissue adhesion so as to create potential implant removal issues.

In one aspect, the improved implant involves the use of non-randomly located biodegradable materials as a part of the drug-containing matrix (or core) to eliminate and/or to lessen an undesired drug "burst." These non-randomly located biodegradable materials also are intended to assist in the "flattening" out and/or the extension of drug delivery over a period of 3, 7, 14, 30 or more days.

Thus, for example, by selecting the location of these biodegradable materials and/or barriers, it is possible to intentionally create mini-chambers of drug materials that are designed to regulate the delivery of the drug materials to the patient. The ability to create non-randomly located barriers is enhanced by the use of 3-D printing processes.

More specifically, these biodegradable materials can regulate the delivery rate of a drug material during the term of the implant in order to adjust the drug delivery levels to the needs of the patient. They also can regulate the delivery of more than one drug material to the patient.

As will be explained more fully in the description of the embodiments, the invention provides, inter alia, a very flexible way to create the appropriate (i) matrix channel size, (ii) drug material(s) amount in the matrix and (iii) drug delivery rate through the selection of non-randomly located biodegradable barriers.

In very broad terms, this may be accomplished (for example) by creating multiple mini-chambers of drug materials via the use of non-randomly located biodegradable materials as barriers within the channels of the matrix. The use of channels to deliver drug materials is employed in existing implants. However, the concept of non-randomly located mini-chambers within the channels that are created by non-random biodegradable barriers is believed to be novel.

Thus, in the preferred approach, the improved implants serially "unlock" individual non-random mini-chambers as the biodegradable materials are absorbed into the body. In a sense, the mini-chambers create a "time release" mechanism for the drug materials that may be designed to meet the particular needs of specific patients.

Furthermore, in another aspect, the improved implant may employ the use/release of anticoagulant materials to avoid or lessen clotting problems. The placement of the anticoagulant materials (i) on and/or in the coating, (ii) within the matrix and/or (iii) on or in the implant opening(s) provides a novel structure for addressing clotting problems. A clotting problem may be especially harmful in, near to or within the opening area of the implant.

These two aspects (improved drug delivery and anti-clotting) may be used separately or together.

In yet another aspect, an improved implant may be achieved by the use of novel impermeable materials in the coating(s) and/or as a part of the matrix. These novel materials (which are described below) may be used alone or in combination with prior art impermeable materials. These novel materials are intended, inter alia, to provide a stronger and/or more abuse-resistant coating and to better ensure proper drug release patterns.

BACKGROUND

The prior art discloses the uses of implants for mammals having (a) a coating, (b) a matrix (containing drug material and, sometimes, other materials) and (c) one or more openings in the matrix and/or coating through which the drug materials reach the body. The prior art also teaches that tiny channels exist in the matrix/core wherein the drug materials are held prior to implanting. For example, the prior art teaches that the drug material may be "mixed" with matrix materials to create those channels. After being implanting, the channels in the prior art matrix (or the mixture of drug and biodegradable materials when dissolving) result in the release of the drug materials to the mammalian patient.

Applicant is an inventor of the subject matter disclosed and claimed in a U.S. application filed on Mar. 12, 2013, Ser. No. 13/796,875 (now Publication No. US 2014/0099351, published on Apr. 10, 2014)—as well as (a) the later corresponding PCT application filed on Oct. 4, 2013 and (b) the earlier provisional application Ser. No. 61/709,586, filed Oct. 4, 2012. The disclosures in all three of these applications are incorporated herein by reference. However, this application does not claim priority thereto because this provision application is directed to different inventions.

The foregoing Publication identifies a number of other patents, applications, articles, materials and devices in, inter alia, paragraphs 0002, 0004, 0005, 0007, 0008, 0039 and 0056. These references describe a wide variety of materials that can be used in this improved medical implant. Again, these references are expressly incorporated herein but no claim of priority is made to them.

In addition, Axxia Pharmaceuticals has obtained U.S. Pat. Nos. 5,633,000; 5,858,388; and 6,126,956 and it has filed pending U.S. Ser. Nos. 12/738,113; 61/533,131; 13/264,813; and 13/606,795 with respect to certain implant products and various processes for making those products. Similarly, these references are expressly incorporated herein but no claim of priority is made to them.

Significantly, none of these references describe or suggest, inter alia, the use of non-randomly located biodegradable materials and/or barriers in a mammalian implants to create mini-chambers that are intended to regulate drug delivery from a matrix. Likewise, none of these references describe or suggest, inter alia, the use of anticoagulant materials as a part of the implant for anti-clotting purposes. Finally, none of these references disclose the novel impermeable materials disclosed below for use in coatings and/or the matrix.

SUMMARY

It is a general intention of this provisional application to set forth an improved medical implant device for mammals wherein the use of biodegradable materials in the drug-containing matrix creates non-random biodegradable barriers and/or drug mini-chambers in the matrix channels which have the effect of reducing or regulating the initial drug "burst" and/or of "flattening" out (or otherwise "adjusting") the drug delivery levels during a 3 or more day time period. It is another general intention of this application to set forth an improved drug implant wherein anticoagulant materials are a feature of the implant device and are intended to regulate and/or maintain the flow of drug material delivery by reducing and/or eliminating clotting. It is not necessary that both general intentions be implemented in all improved implants.

One suspected cause of the drug "burst" phenomena is capillary action. In other words, it is suspected that capillary action in an implant device is strongest when the initial/early drug delivery takes place. Thus, this application contemplates the use of, inter alia, non-randomly located biodegradable walls and/or mini-chambers within the matrix channels to regulate and/or inhibit the capillary activity during the initial drug delivery and during subsequent drug delivery.

Moreover, it is suspected that capillary action may have another adverse effect on drug delivery. More specifically, as drug is delivered to the patient from the implant, it is typical for drug delivery to slow down or lessen. Thus, at least some percentage of the drug typically is never delivered to the patient but, instead, remains locked within the implant.

The cause of this slower and/or non-delivery also is suspected to be related to capillary action. In that regard, just as the initial capillary action may draw out too much drug, capillary action likely decreases as the non-biodegradable matrix channels are emptied and the length of the empty channels become longer.

One possible way to address this may issue is to use two or more biodegradable materials in the matrix. The fastest to degrade will typically be the matrix barriers. In that situation one or more slower biodegradable matrix materials may be employed to enhance the capillary action as the drug is emptied from the matrix. Alternatively, the barriers and the other matrix materials may be the same or very similar rapidly biodegradable materials.

Nevertheless, it must be understood that the matrix also may be formed at least in part of non-biodegradable materials wherein the channels contain drug materials and non-randomly located biodegradable barrier materials. In that situation, one may create a single biodegradable barrier along the entire length of the channel wherein the barrier and drug materials are mixed together. Controlled release in that situation may be adjusted by, for example, (a) the selection of the biodegradable materials and/or (b) the % of drug materials in that mixture. In that situation, these adjustments may create separate non-randomly located barriers. However, separate mini-chambers need not always be created by barriers.

Although the improved medical implants and methods of manufacture are deemed to be especially applicable where narcotics or semi-narcotics are being delivered, this invention also contemplates the delivery of non-narcotic drugs (such as contraceptives or other non-narcotic drugs that require a relatively lengthy period of delivery—e.g., 3 days, 7 days, 14 days, 30 days or longer).

As explained above, the improved implant creates non-randomly located biodegradable structures (barriers and/or mini-chambers) within these channels to regulate the flow of the drug materials. The use of these biodegradable structures in the channels can serve a number of purposes—e.g., (a) to partially eliminate and/or to lessen the initial undesired drug "burst"; (b) to assist in the "flattening" out and/or the extension of drug delivery over a period of 3, 7, 14, 30 or more days; and (c) to otherwise regulate the level of drug delivery (either up or down) during the useful life of the implant.

The selection of one or more particular rapid biodegradable materials will depend upon specific period of drug delivery. Obviously, a device delivering drug material for 14 days will likely utilize different biodegradable materials from a device that delivers drug materials for 30 or more days. However, it is believed that the best results will typically require the use of at least one or, in many instances, more than one rapidly biodegradable materials.

The present application also contemplates (but does not require) the use of an impermeable coating over the drug-containing matrix. This coating is intended to limit the drug delivery to mammals via one or more openings in the coating material. Typically (but not always), the impermeable coating is important to provide protection against drug abuse or misuse—especially, where the drug materials are narcotics or semi-narcotics.

The Axxia patents and applications (identified above in the prior art section) set forth various impermeable coating and matrix materials. However, other materials not taught in the prior art may achieve and/or exceed the strength and other benefits of these prior art materials. These novel materials may be used alone or, it is believed preferably, in combination with prior art materials. The novel materials include coating and/or matrix mixtures containing, among other things, (i) carbon fiber materials and/or carbon fiber composite materials, (ii) relatively small amounts of metals, (iii) graphene, (iv) ceramic and/or carbon-ceramic materials and/or (v) mixtures of some or all of (i) to (iv). Although many metals may be employed, titanium is one of the preferred metals due to its strength.

Further, in order to avoid drug delivery problems, the present application also contemplates the use of anticoagulant materials (either with or without the above described barrier structure). These anticoagulant materials can be, inter alia, (a) associated with the outside surface of the implant such as topical application on the exterior of the coating and/or in capillaries created in the exterior layers of the coating, (b) on the surfaces of the opening(s) and/or on the surfaces of the opening sidewall within the implant, (c) included as a part of one or more matrix barriers/materials and/or (d) incorporated as a part of the drug materials.

Examples of potential anticoagulant materials include, inter alia, antithrombics and thrombolytics. The particular choice of an anticoagulant material may depend upon factors such as the general type of mammalian patient, the particular implant patient, the drug material being delivered, et cetera. It is anticipated that in the usual situation only relatively very low levels of anticoagulant material will be necessary or desirable.

Typically, only one drug material will be contained in the matrix of the implant. However, the present invention is not intended to be limited to the delivery of just one drug. For example, this application also contemplates situations where the delivery of more than one drug is done simultaneously and/or serially. Similarly, multiple drugs can be delivered together via one opening (simultaneously or serially) or via more than one opening (separately, simultaneously or serially). Thus, for example, the matrix may be loaded like a "multi-decker" device.

Further, the present application contemplates flexibility in the components of the matrix. For example, the matrix may be made of a combination of (a) at least one non-biodegradable material and/or at least one biodegradable material and (b) at least one drug material.

Thus, for example, the matrix may be made without any non-biodegradable materials from (a) two or more biodegradable materials (i) with at least one used for the matrix barrier(s) and (ii) with at least one used for the matrix non-barrier(s), and (b) at least one drug material. In that regard, the non-barrier biodegradable material normally will be designed to dissolve/degrade at about the same or a slightly slower rate than the barrier biodegradable material. In addition, if more than two biodegradable materials are used in the matrix, then different rates of dissolution/degradation may be used to create or adjust the desired drug delivery levels. Finally, if a biodegradable material is used as the coating, then it is preferable (but not always required) that it should degrade at a significantly lower rate than any biodegradable material in the matrix.

Examples of relatively rapid medical biodegradable matrix materials are identified, inter alia, in "Biodegradable Polymer Implants to Treat Brain Tumors," Journal of Controlled Release 74 (2001) 63-67; "An Introduction to Biodegradable Polymers as Implant Materials," White Paper from Inion OY (2005); Lendlein et al, "Handbook of Biodegradable Polymers," (2011); and Caballero, et al, "Critical Evaluation of Biodegradable Polymers Used in Nanodrugs," International Journal of Nanomedicine (August 2013).

Examples of prior art non-biodegradable matrix materials and prior art impermeable coating materials include, inter alia, EVA, TPU, silicone and other materials well known to those of ordinary skill in the art. Examples of novel impermeable materials (i.e., non-biodegradable materials) for the coating and/or matrix are taught above in this specification.

These novel materials or the prior art materials also can be used, inter alia, to create one or more nanotubes or nanostructures within the matrix for the delivery of one or more drugs. The nanotubes/nanostructures also can be used in the coating to deliver, for example, anticoagulant or other drug materials. In that regard, carbon fiber (alone or with a metal), ceramic materials and/or graphene are preferred nanotube/nanostructure materials. Although 3-D printing is a preferred technique, other methods may be used to create the nanotubes and/or nano structures.

Examples of drug materials include both non-narcotic as well as narcotic drugs. In essence, there is no limitation on the type of drugs that may be used in the improved implant so long as, in general, they are (i) capable of being used in mammalian implant devices and (ii) capable of delivery from such an implant for a period of 3 or more days. Due to implant size constraints, it is likely that the maximum term for drug delivery from an implant for humans is 60-90 days. However, larger mammals may be able to accept a larger implant device having a longer period of drug delivery. Conversely, smaller animals will typically accept a smaller implant with a shorter period of drug delivery.

Examples of narcotic drug materials include, inter alia, opiates, opioids, morphine, codeine, hydrocodone, oxycodone, hydromorphone, oxymorphone, probuphine and fentanyl. See, also, U.S. Pat. No. 8,114,383 for a partial listing of narcotic drugs.

It is believed that (i) a 3-D printing process or (ii) a 3-D printing process combined with other known implant manufacturing process(es) are the best methods of manufacture for the improved implants disclosed herein because, for example, 3-D printing processes can be more readily used to create channels/chambers. However, this application is not limited to an improved implant made only from 3-D printing steps.

As a result, this application also contemplates the manufacture of the improved implant via processes other than a 3-D printing process and also processes combined with a 3-D printing process—e.g., extrusion to create the matrix or the coating; and shrink wrap to create a coating. In those manufacturing processes, the drug materials and the biodegradable materials may be blended/mixed together (i) in differing proportions in different areas of the matrix (for example, via extrusion) or (ii) in non-randomly located biodegradable barrier portions containing no drug materials also may be created (for example, via extrusion) during manufacture.

As described in applicant's Ser. No. 13/796,875 (now Publication No. US 2014/0099351), there are numerous distinct advantages with 3-D printing processes in view of the more precise placement and distribution of material and structures in implants. In that regard, 3-D printing processes are preferred to create the non-randomly located biodegradable barriers and to effectively use anticoagulant materials with an implant.

Nevertheless, for example, the ability to create (in terms of the present invention) the non-randomly located biodegradable barriers in the matrix, the mini-chambers in the matrix channels and/or anticoagulant usage exists with respect to non-3-D printing processes for at least some portions of the improved implant—e.g., extrusion of a layer, then the removal of a portion of the layer, and then the inkjet deposition of a liquid material into the area where material was removed.

During the prosecution of applicant's Ser. No. 13/796,875 (now Publication No. US 2014/0099351), one reference has been cited to date. More specifically, please see Weigang, et al, "The Controlled-releasing Drug Implant based on the Three Dimensional Printing Technology," Journal of Wuhan University of Technology-Materials Sci. Ed., Vol 24, No. 6, pages 977-981 (December 2009). However, that reference does not disclose or suggest the inventions of this nonprovisional application.

DETAILED DESCRIPTION

Figure 1:
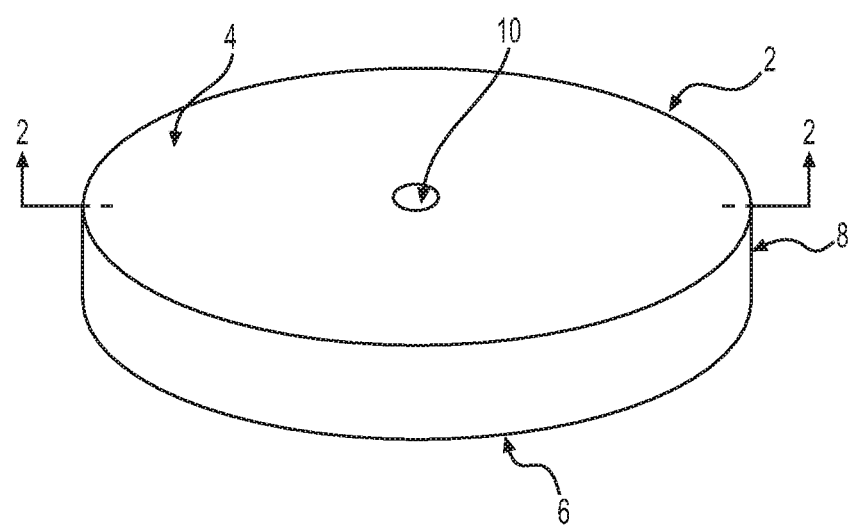
FIG. 1 is a perspective view of an exemplary prior art product.

FIG. 1 shows a very basic structure of a prior art subcutaneous medical implant device. Implant disc 2 consists of a top 4, a bottom 6 and an outside wall 8. It also has an opening 10 that is used for drug delivery. The size of opening 10 and the number of openings may vary.

Line 2-2 will be used in the remaining Figures to illustrate various internal structures of the prior art implants and of the improved implants disclosed in this application. However, please understand that these Figures are not intended to cover all of applicant's improved implant structures.

In addition, for example, the Figures are not representative of the number of layers of materials in an implant. Also, although the matrix materials are shown in regular shapes, they need not have such a regular shape—e.g., the channel may have a curved or irregular shape, and it have different heights/widths (such as lower/narrower near the opening and expanded/broader thereafter, or vice versa).

In that regard, the preferred 3-D printing process is believed to provide, inter alia, the capability and flexibility to design different matrix channel shapes, sizes, designs, et cetera. If non-3-D printing processes (such as extrusion) are used to make the matrix, the channels and barriers are likely to be more arbitrarily configured. Nevertheless, non-3-D processes (such as hot-melt casting, extrusion and shrink wrap) may be used in the formation of some (or all) of the improved implant.

FIG. 1 shows a generally cylindrical implant device. However, the shape of the implant in this embodiment (and in all other embodiments) may be modified to whatever shape is desirable. In other words, a particular exterior shape of the implant is not critical to the improved implant of this application.

In looking at the Figures, it should be borne in mind that the structures are not drawn to scale. Instead, they are drawn in a manner to illustrate the general subject matter of this application. Thus, the relative sizes/shapes/dimensions of the coating, matrix materials, matrix channels, matrix barrier materials, drug materials, anticoagulant channels/materials and the like are not intended to be realistic.

Figure 2:
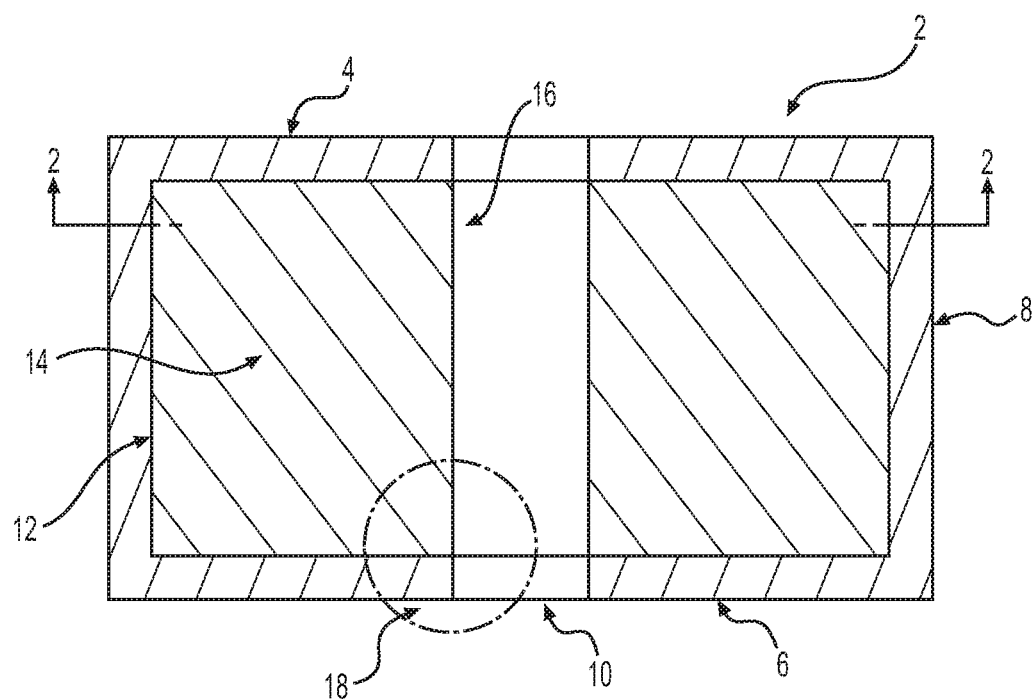
FIG. 2 is a cross-sectional view of the product in FIG. 1 along line 2-2.

FIG. 2 shows the very basic structure of the prior art implant along line 2-2 of FIG. 1. More specifically, an impermeable coating 12 generally surrounds matrix 14. In that regard, the coating must be impermeable in terms of (a) prohibiting the flow of drug materials and (b) having a relatively high breaking strength.

Opening 10 extends all of the way through implant 2. As a result, edges of the coating and matrix create sidewalls 16 to the opening.

Although the opening in this and all other embodiments is shown to extend entirely through the implant, this is not always necessary. Moreover, it should be understood that there may be one or more openings that extend fully or only partially through the implant.

Circle 18 in FIG. 2 will be used in illustrate the applicant's embodiments disclosed below in FIGS. 3 to 7. Circle 18 is intended to create a somewhat microscopic view of a portion of the improved implant so as to help explain some of the structures, functions and purposes of the subject matter of this application.

More specifically, in one possible situation, the matrix is surrounded by an impervious coating. The matrix is comprised of, inter alia, at least one (1) non-randomly located biodegradable barrier material, (2) non-biodegradable material and (2) drug material. In addition, the matrix and coating have at least one opening for drug delivery. Likewise, the matrix should have one or, preferably, more channels for drug delivery. Further, it also is contemplated that the drug material may or may not be mixed with the barrier material. Further design options are discussed below.

Figure 3:
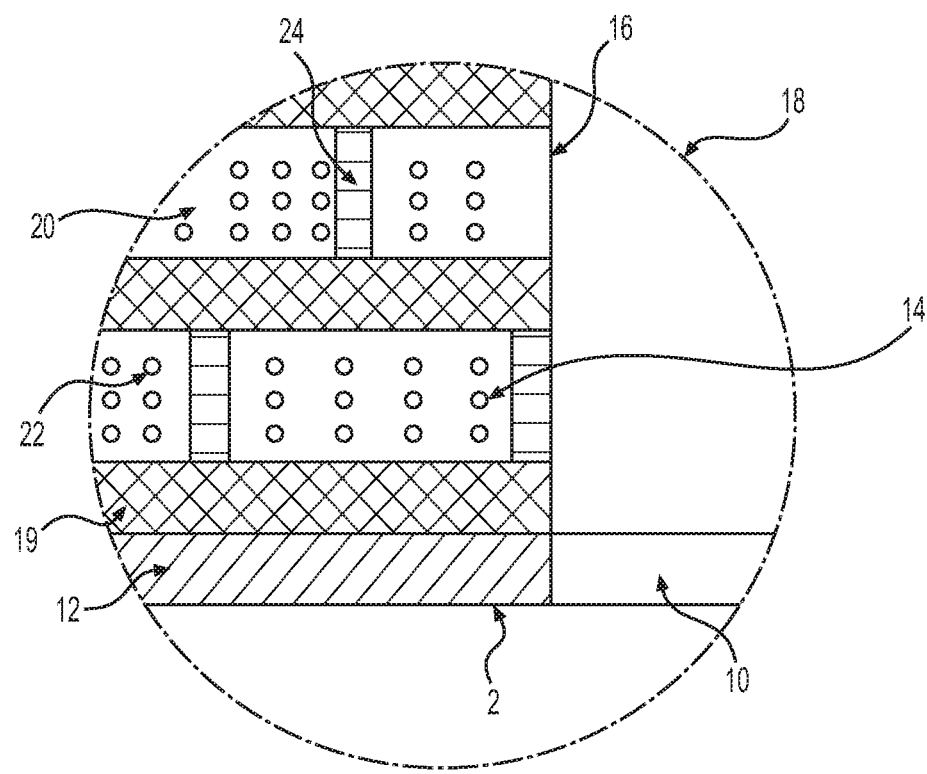
FIG. 3 is a cross-sectional view of applicant's first embodiment with a close-up view via circle 18.

FIG. 3 illustrates some of the novel aspects of this application. Circle 18 of this Figure shows a representative close-up view of one section of the implant device 2 for the first embodiment.

Again, it should be understood that the size, shape, location and structure of the channel(s) in the matrix may be configured in many different ways to ensure the desired drug delivery mechanism. Thus, the present invention is intended to provide great flexibility in drug delivery, especially when 3-D printing processes are used to make some or all of the matrix layers.

More specifically, the implant 2 (partially shown) in FIG. 3 has an opening 10 (partially shown), an opening sidewall 16 (partially shown), an impervious coating 12 (partially shown) and a matrix 14 (partially shown). In that regard, matrix 14 contains several elements. For example, the matrix 14 in this embodiment includes a non-biodegradable matrix portion 19 having channels 20 containing at least two different materials. The different materials in the channels of this embodiment are drug material 22 and biodegradable barrier 24.

The biodegradable barrier material 24 for this embodiment (and at least some other embodiments) may be the same as or different from other biodegradable materials in the matrix. Furthermore, it is expressly contemplated that the barriers may be made of different biodegradable materials and may be of different thicknesses or other dimensions. Thus, for example, different biodegradable materials and thicknesses may be utilized to provide enhanced drug release timing options.

As shown in FIG. 3, barriers 24 can be placed in various locations within the drug containing channels 20. For example, one or more biodegradable barriers 24 can be created at or near opening sidewall 16 to moderate the initial drug burst phenomena. Barriers 24 also may be placed in other locations in channel 20 to create mini-chambers for drug materials. As explained above, these biodegradable barriers are structures used to regulate the time and amount of drug release.

It is expressly contemplated (but not required) that the barriers be staggered in the various channels so that the initial burst of a mini-chamber in one channel is somewhat or largely cancelled out by the drug delivery from the mini-chambers of other channels. This staggering approach may be used from the beginning to the end of the drug delivery.

In addition, in a preferred embodiment, the non-randomly located biodegradable barriers may be created at the end of every channel at the opening sidewall. This will avoid any premature release of drug material prior to implanting.

Likewise, the drug delivery may be regulated by the use of different thicknesses of the barriers. Alternatively, or in addition, the barriers may be made of different biodegradable materials so that drug delivery may be regulated in that way as well. Finally, another approach is regulate drug delivery is to incorporate some drug material into the barriers (especially in barriers located at the opening sidewalls).

As previously discussed, drug material 22 may be one or more different types of drugs. Thus, for example, one or more types of drug material may be used in a first group of mini-channels and other types of drug material may be used in later mini-chambers or in different channels. Alternatively, the %'s of drug materials may be varied in particular mini-chambers/channels. The ability to flexibly employ various drugs and various drug levels in different mini-chambers/channels is believed to be enhanced by 3-D printing processes.

In a second embodiment, the matrix is surrounded by an impervious coating and the matrix is comprised of, inter alia, at least one (1) non-randomly located biodegradable barrier material, (2) coating material used as a non-biodegradable material and (3) drug material. In addition, the matrix and coating have at least one opening for drug delivery. Once again, the drug material may or may not be mixed with the barrier material. Further design options are discussed elsewhere in this application.

Figure 4:
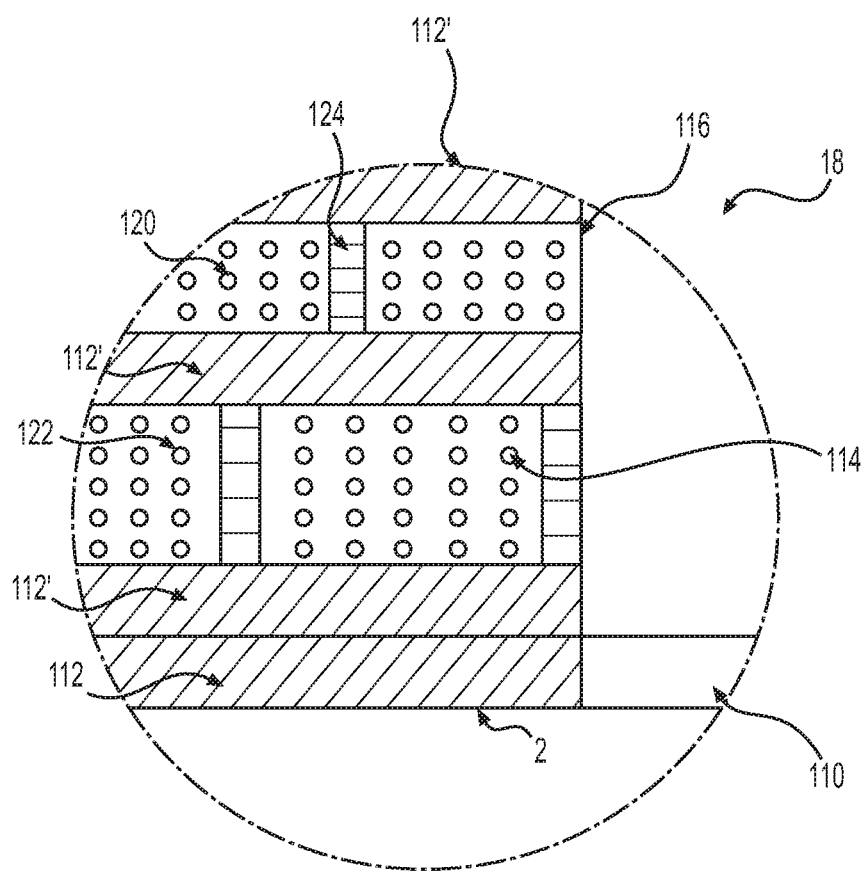
FIG. 4 is a cross-sectional view of applicant's second embodiment with a close-up view via circle 18.

FIG. 4 illustrates some of the other novel aspects of this application. Circle 18 of this Figure shows a representative close-up view of one section of the implant device 2 for the second embodiment.

More specifically, the implant 2 (partially shown) has an opening 110 (partially shown), an opening sidewall 116 (partially shown), an impervious coating 112 (partially shown) and a matrix 114 (partially shown). Once again, matrix 114 contains several elements. For example, the matrix 114 in this embodiment includes a non-biodegradable matrix portion 112' made from the same impervious materials as coating 112. In addition, the non-biodegradable matrix material 112' has channels 120 containing different materials. The different materials in this embodiment are drug material 122 and non-randomly located biodegradable barriers 124.

As shown in FIG. 4, barriers 124 can be placed in various locations within the drug containing channels 120. For example, one or more biodegradable barriers 124 can be created at or near opening sidewall 116 to moderate the initial drug burst phenomena. Barriers 124 also may be placed in other locations in channel 120 to create mini-chambers for drug materials.

As previously discussed, drug material 122 may be one or more different types of drugs.

In addition to the above concepts, the use of only biodegradable materials in the matrix may be beneficial in the delivery of the drug material because it may lessen the % of drug materials that are remain in the implant device when (a) the drug delivery is substantially completed and/or (b) the implant is removed. For example, the capillary action effect in terms of drug delivery may decrease as the distance from the opening(s) increase. This may inhibit the delivery of all drug materials in the implant to the patient.

Thus, in a third embodiment, the matrix surrounded by an impervious coating and the matrix is comprised of, inter alia, of (1) at least two different biodegradable materials and (2) at least one drug material. The two biodegradable materials typically have different rates of biodegradability so as to regulate/control drug delivery. In addition, the matrix and coating have at least one opening for drug delivery. As indicated previously, a drug material may or may not be mixed with the barrier material. Further design options are discussed elsewhere in this application.

For example, one option is for one or more drug materials to be mixed with a biodegradable material in a matrix barrier and/or in the biodegradable material of the matrix.

In addition, another option is to form the barriers from different and/or multiple biodegradable materials. This is yet another way in which drug delivery may be regulated by non-randomly located biodegradable materials.

Figure 5:
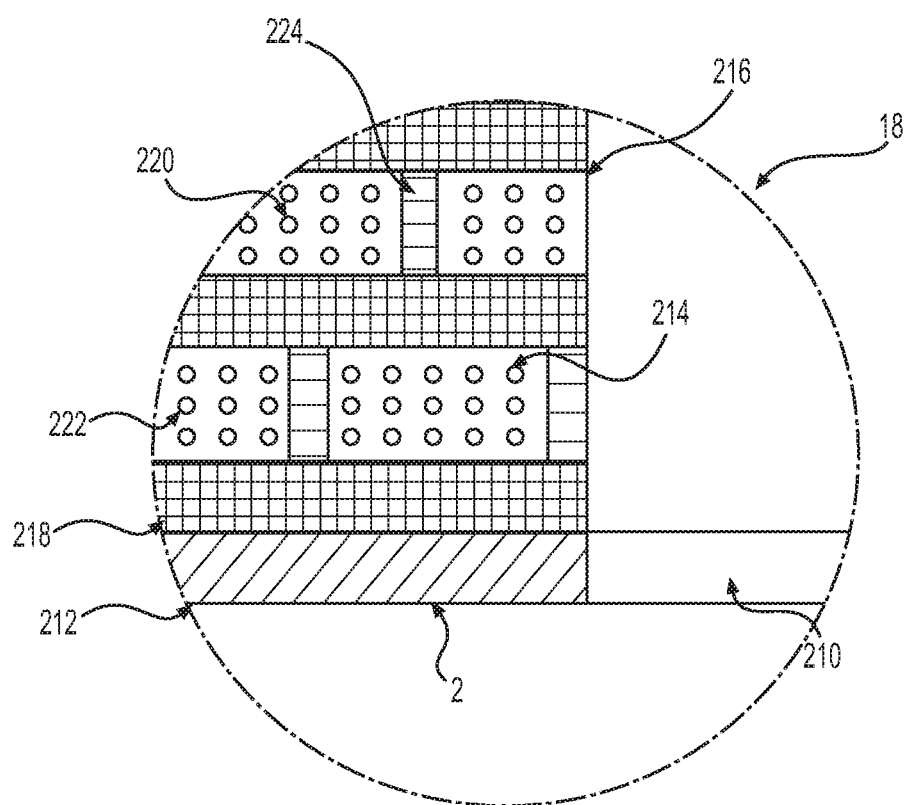
FIG. 5 is a cross-sectional view of applicant's third embodiment with a close-up view via circle 18.

FIG. 5 illustrates some of the other novel aspects of this application. Circle 18 of this Figure shows a representative close-up view of one section of the implant device 2 for the third embodiment.

More specifically, the implant 2 (partially shown) has an opening 210 (partially shown), an opening sidewall 216 (partially shown), an impervious coating 212 (partially shown) and a matrix 214 (partially shown). In that regard, matrix 214 contains several elements. For example, the matrix in this embodiment includes at least two different biodegradable materials 218 and 224. The matrix also has channels 220 containing different materials. The different materials in this embodiment are drug material 222 and biodegradable barrier 224.

As shown in FIG. 5, non-randomly located barriers 224 may be placed in various locations within the drug containing channels 220. For example, one or more biodegradable barriers 224 can be created at or near opening sidewall 216 to moderate the initial drug burst phenomena. Barriers 224 also may be placed in other locations in channel 220 to create mini-chambers for drug materials.

As previously discussed, drug material 222 may be one or more different types of drugs.

In a fourth embodiment, the matrix does not have an impervious coating. Instead, the coating also is biodegradable.

In that situation, the matrix is comprised of, inter alia, of (1) at least two different biodegradable materials and (2) at least one drug material. The two biodegradable materials in the matrix have different rates of biodegradability so as to regulate/control drug delivery.

Furthermore, because the coating is biodegradable, the coating preferably should have a much lower/slower rate of biodegradability than the biodegradable materials in the matrix so that the drug delivery is maintained only through the one or more original openings in the coating.

As indicated previously, the drug material may or may not be mixed with the barrier material. In addition, the matrix and coating have at least one opening for drug delivery.

Figure 6:
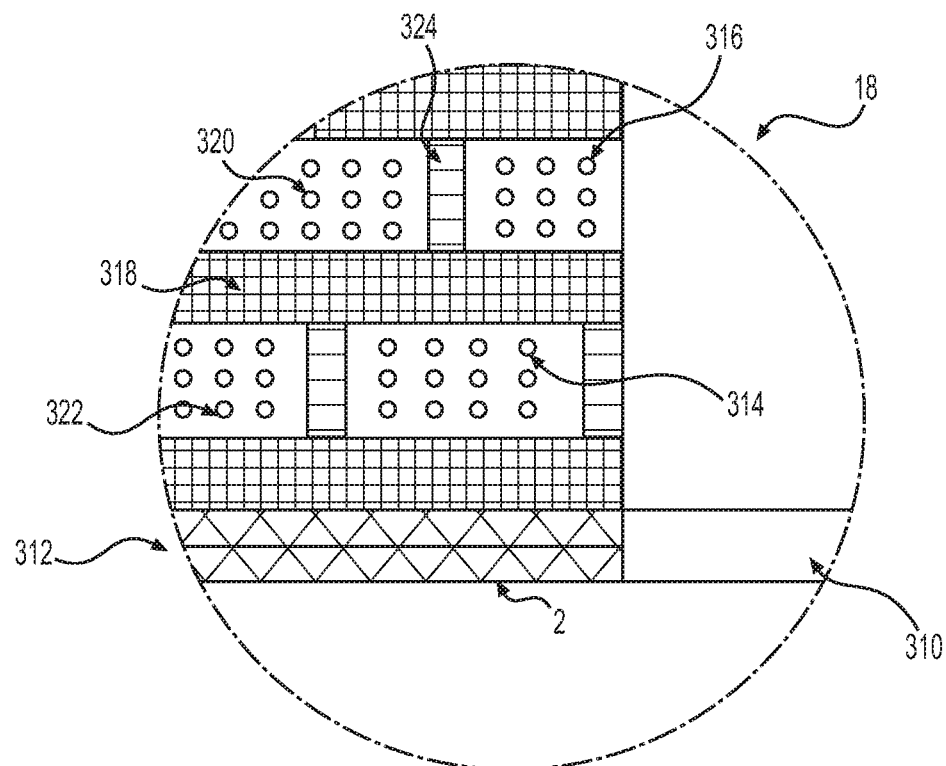
FIG. 6 is a cross-sectional view of applicant's fourth embodiment with a close-up view via circle 18.

FIG. 6 illustrates some of the other novel aspects of this application. Circle 18 of this Figure shows a representative close-up view of one section of the implant device 2 for the fourth embodiment.

More specifically, the implant 2 (partially shown) has an opening 310 (partially shown), an opening sidewall 316 (partially shown), a biodegradable or semi-biodegradable coating 312 (partially shown) and a matrix 314 (partially shown). In that regard, matrix 214 contains several elements. For example, the matrix 314 in this embodiment includes a biodegradable matrix portion 318 that has channels 320 containing different materials. The different materials in this embodiment are drug material 322 and biodegradable barrier 324.

As shown in FIG. 6, barriers 324 can be placed in various locations within the drug containing channels 320. For example, one or more biodegradable barriers 324 can be created at or near opening sidewall 316 to moderate the initial drug burst phenomena. Barriers 324 also may be placed in other locations in channel 320 to create mini-chambers for drug materials.

As previously discussed, drug material 322 may be one or more different types of drugs.

In a fifth embodiment, the previous four embodiments are modified so as to also incorporate the use of anticoagulant materials to avoid and/or limit blood clotting when the device is implanted. The anticoagulant materials may be applied to various parts of the implant. For example, the anticoagulant material may be, inter alia, (i) applied to various areas of the coating such as on top of the coating or as a part of the exterior of the coating, (ii) applied to one or more surfaces of the opening(s) and/or (iii) mixed with the matrix materials.

Figure 7:
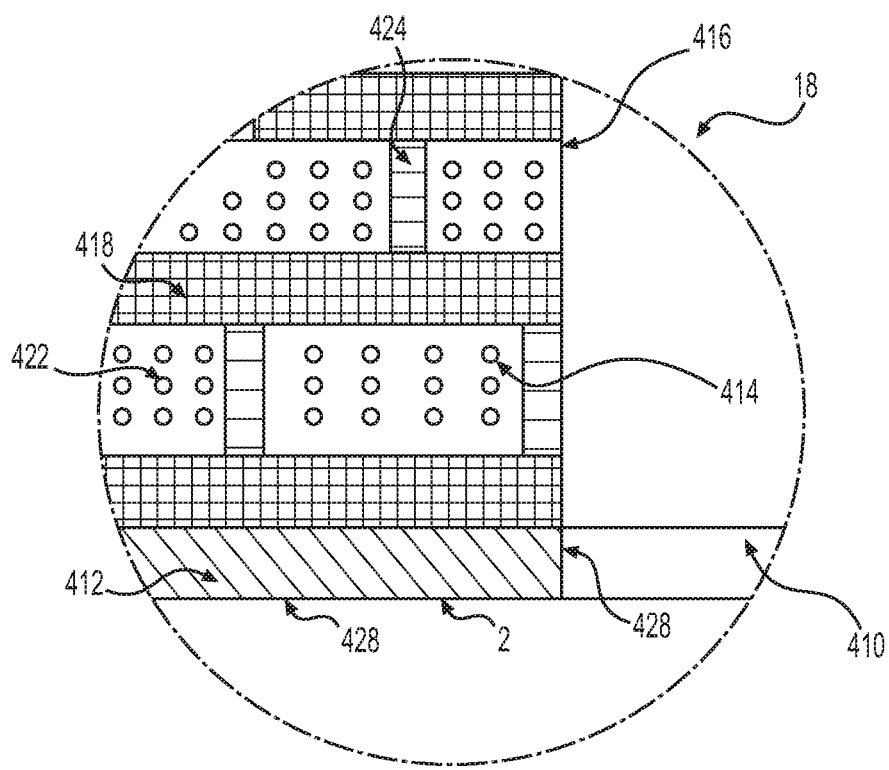
FIG. 7 is a cross-sectional view of applicant's fifth embodiment with a close-up view via circle 18.

The fifth embodiment is illustrated in FIG. 7. There, anticoagulant material is applied topically to various locations (such as locations 428) on coating 412. Alternatively, anticoagulant material can be topically applied to surfaces (such as opening sidewall surface 416) of opening 410. And/Or, the anticoagulant material may be mixed with drug material 422, matrix material 418 and/or barriers 324 within matrix 414.

In a sixth embodiment (not shown in a Figure), anticoagulant material may be incorporated within a portion of the coating. In one approach, the anticoagulant material may incorporated into or on top of the coating by 3-D printing methods (via, for example, very small channels opening on the surface of the coating) or by non-3-D printing methods (via, for example, a separate biodegradable material located on the outside surface of the coating).

In a seventh embodiment (also not shown in a Figure), the matrix is formed as a mixture of materials—i.e., without defined channels. Although a 3-D printing process may be used, this matrix structure also may be obtained by a non-3-D printing process.

In that seventh embodiment situation, it is envisioned that the materials (e.g., the composition and % mixtures) will vary throughout the matrix in order to reduce the "initial burst," to maintain a more level of drug delivery (or, alternatively, to adjust the rate of drug so that at certain desired times drug material is delivered in a higher or lower %) and/or to provide anticoagulant material. Thus, this is another way in which the use of different matrix material compositions may be formed (e.g., by extrusion, partial material removal and subsequent liquid deposition) so as to create so-called non-randomly located biodegradable materials/barriers having different compositions which are intended to regulate the delivery of drug materials. A coating material(s) may be subsequently applied to the matrix (via, e.g., shrink wrap) and, thereafter, one or more openings may be created in the implant.

In another approach, the type of biodegradable material may vary with, in one approach, a slower dissolving rate biodegradable material being close to the opening and with different biodegradable material having faster dissolving rates farther from the opening. Thus, an initial level of drug delivery may be established and then a higher rate of drug delivery is established during a subsequent drug delivery period(s).

In addition to or as an alternative, a lower % of drug material may be located closer to the implant opening to avoid/lessen the initial drug burst. Thus, the present invention contemplates that the % of the drug material may be varied (e.g., increased and/or decreased) as the distance increases from the opening.

Moreover, in addition to or as yet another alternative, the anticoagulant material may be located in the matrix mixture just in the area nearer to the opening or that material may be included, for example, in lower, higher or the same dosages elsewhere in the biodegradable matrix. In that regard, it may be desirable to have anticoagulant material delivered at a time relatively close to the removal of the implant.

Furthermore, the invention is intended to provide an improved implant where the matrix barrier materials and drug materials are varied—in terms of locations materials and %. The exact choice of biodegradable materials and the % concentration at different locations may be adjusted depending, for example, upon the drug material(s) to be delivered to the patient.

As indicated above, the present invention covers the situation where the 3-D printing method is used to create all or just a portion of the implant device—e.g., at least only 3 or more layers of the matrix. However, the invention also contemplates the situation where one or more layers of the matrix and/or coating are created by other methods. Further, the present invention also envisions processes that deposit layers having the same or different thicknesses.

The seventh embodiment also may be used with distinct walls and/or distinct channels as shown in other embodiments. In other words, modifications and/or variations may be readily made to all embodiments without departing from the spirit or scope of my inventions.

Finally, in the situation where more than one drug material is desired, this invention also envisions the use of one or more openings to deliver these different drugs either separately, serially or together in terms of times and locations.

Some of the potential advantages resulting from the use of the above non-randomly located biodegradable barriers and/or anticoagulant materials include at least the following:

1. The use of non-randomly located biodegradable barrier structures may permit a higher % of drug materials in the implant to be delivered to the patient; and
2. The use of non-randomly located biodegradable barrier structures may permit a more "flat" or "steady" level of drug delivery; and
3. Blood clotting may be reduced by incorporating anticoagulant material in or on the implant; and
4. Removal of the implant may be easier if anticoagulant materials are used; and
5. The timing and level of drug delivery may be adjusted by the use of the biodegradable barrier structures and/or other biodegradable matrix materials having different compositions and dimensions; and
6. The use of non-randomly located biodegradable barrier structures may enhance the timed delivery of two or more drugs.

These embodiments and potential advantages are intended to merely be examples. As may be readily appreciated by those of ordinary skill in the manufacture and design of medical implant art, the present inventions can be practiced in ways other than as specifically disclosed herein. Thus, while the inventions have been described generally and with respect to certain preferred embodiments, it is to be understood that the foregoing and other modifications and variations may be made without departing from the scope or spirit of my inventions.

The invention claimed is:

1. An implantable medical drug delivery device for delivering a therapeutic drug to a patient for at least a desired drug delivery period, the device comprising at least one matrix having a non-homogenous matrix mixture of at least two different types of drug materials,
    wherein one of said at least two types of drug materials is the therapeutic drug that is not an anticoagulant and has a first total dosage amount within said at least one matrix, wherein an other type of drug material within said at least one matrix is an anticoagulant drug and has a second total dosage amount within said at least one matrix, wherein the first total dosage amount of said therapeutic drug is higher than said second total dosage amount of said anticoagulant drug, wherein said at least two types of drug materials have varied concentrations within said at least one matrix, wherein the lower second total dosage amount and varied concentration of said anticoagulant drug regulate both blood clotting and a delivery rate of said therapeutic drug to the patient, and wherein the anticoagulant drug primarily lessens formation of blood clotting near, on or within said device.

2. The device according to claim 1, wherein said device further comprises a coating over at least a part of said at least one matrix.

3. The device according to claim 1, wherein said varied concentrations of said at least two types of drug materials result in a more flattened drug delivery over the desired drug delivery period.

4. The device according to claim 1, wherein said varied concentrations of the therapeutic drug and the anticoagulant drug decrease an initial drug delivery burst of said therapeutic drug to the patient.

5. The device according to claim 1, wherein said anticoagulant drug reduces a remaining amount of said therapeutic drug within said device after the desired drug delivery period.

6. An implantable medical drug delivery device for delivering more than one therapeutic drug to a patient for at least a desired drug delivery period, the device comprising at least one matrix having a non-homogenous matrix mixture of at least two different types of drug materials, wherein said at least one matrix mixture comprises:

the more than one therapeutic drug having a first total combined dosage amount, wherein the more than one therapeutic drug is not an anticoagulant; and at least one anticoagulant drug having a second total dosage amount, wherein the first total combined dosage amount of the more than one therapeutic drug is higher than said second total dosage amount of said at least one anticoagulant drug, wherein said at least one anticoagulant drug has a varied concentration within said at least one matrix, wherein the lower second total dosage amount and varied concentration of said at least one anticoagulant drug regulate both blood clotting and a delivery rate of said more than one therapeutic drug to the patient, and wherein the at least one anticoagulant drug primarily lessens formation of blood clotting near, on or within said device.

7. The device according to claim 6, wherein said device further comprises a coating over at least a part of said at least one matrix.

8. The device according to claim 6, wherein said varied concentration of said at least one anticoagulant drug results in a more flattened drug delivery over the desired drug delivery period.

9. The device according to claim 6, wherein said varied concentration of said at least one anticoagulant drug decreases an initial drug delivery burst of said more than one therapeutic drug to the patient.

10. The device according to claim 6, wherein said anticoagulant drug reduces a remaining amount of said more than one therapeutic drug within said device after the desired drug delivery period.

11. An implantable medical drug delivery device for delivering at least one therapeutic drug to a patient for at least a desired drug delivery period, the device comprising at least one matrix having a non-homogenous mixture of at least two different types of drug materials, wherein said at least one matrix mixture comprises:

the at least one therapeutic drug having a first total combined dosage amount, wherein the at least one therapeutic drug is not an anticoagulant; and more than one anticoagulant drug having a second total combined dosage amount, wherein the first total combined dosage amount of said at least one therapeutic drug material is higher than said second combined total dosage amount of said more than one anticoagulant drug, wherein said more than one anticoagulant drug has a varied concentration within said at least one matrix, wherein the lower second total dosage amount and varied concentration of said more than one anticoagulant drug regulate both blood clotting and a delivery rate of said at least one therapeutic drug to the patient, and wherein the more than one anticoagulant drug primarily lessens formation of blood clotting near, on or within said device.

12. The device according to claim 11, wherein said device further comprises a coating over at least a part of said at least one matrix.

13. The device according to claim 11, wherein said varied concentration of said more than one anticoagulant drug results in a more flattened drug delivery over the desired drug delivery period.

14. The device according to claim 11, wherein said varied concentration of the more than one anticoagulant drug decreases an initial drug delivery burst of said at least one therapeutic drug to the patient.

15. The device according to claim 11, wherein said more than one anticoagulant drug reduces a remaining amount of said at least one therapeutic drug within said device after the desired drug delivery period.

\* \* \* \* \*